ID [19]

[11] 4,262,938
[45] Apr. 21, 1981

[54] COLOR-DEVELOPING SHEET FOR PRESSURE-SENSITIVE RECORDING SHEETS

[75] Inventors: Akihiro Yamaguchi; Tadashi Kobayashi, both of Yokohama; Kenzaburo Yamuguchi, Kawasaki; Hisamichi Murakami, Yokohama; Noboru Yamato, Tokyo; Akira Hasegawa, Tokyo, all of Japan

[73] Assignees: Mitsui Toatsu Chemicals, Incorporated; Jujo Paper Co., Ltd., both of Tokyo, Japan

[21] Appl. No.: 68,580

[22] Filed: Aug. 22, 1979

[30] Foreign Application Priority Data

Oct. 11, 1978 [JP] Japan .................. 53-124753
Feb. 24, 1979 [JP] Japan .................. 54-21017

[51] Int. Cl.³ .................. B41M 5/16; B41M 5/22
[52] U.S. Cl. .................. 282/27.5; 427/150; 427/151; 428/307; 428/341; 428/342; 428/537; 428/914
[58] Field of Search .................. 106/21; 282/27.5; 427/150, 151; 428/307, 411, 537, 913, 341, 342

[56] References Cited
FOREIGN PATENT DOCUMENTS 49-10856  3/1974  Japan .................. 282/27.5
52-1329   1/1977  Japan .................. 282/27.5

Primary Examiner—Bruce H. Hess
Attorney, Agent, or Firm—Sherman & Shalloway

[57] ABSTRACT

A color-developing sheet for pressure-sensitive recording sheets, said sheet comprising as a color-developing agent at least one 2,2'-bisphenolsulfone nickel salt selected from compounds of the following formula

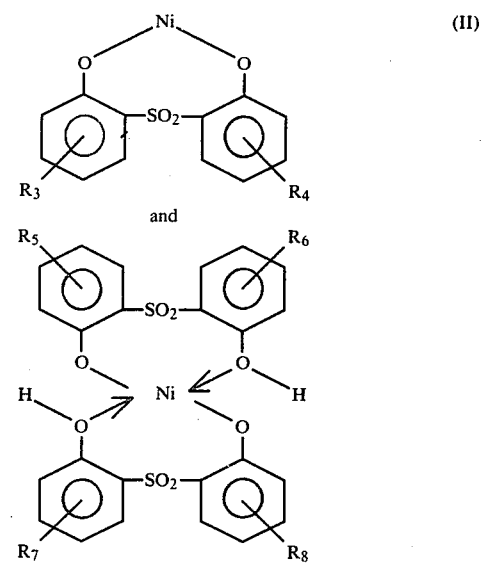

wherein $R_3$, $R_4$, $R_5$, $R_6$, $R_7$ and $R_8$ are identical or different, and represent a hydrogen atom, a halogen atom, an alkyl group containing 1 to 10 carbon atoms, a cycloalkyl group containing 3 to 10 carbon atoms, an aralkyl group containing 7 to 11 carbon atoms, or a phenyl group, or a mixture of at least one 2,2'-bisphenolsulfone nickel salt of the above formulae (II) and (III) and at least one 2,2'-bisphenolsulfone zinc salt of the following formula

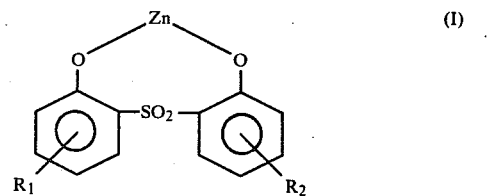

wherein $R_1$ and $R_2$ are the same as $R_3$ through $R_8$ defined above.

18 Claims, 1 Drawing Figure

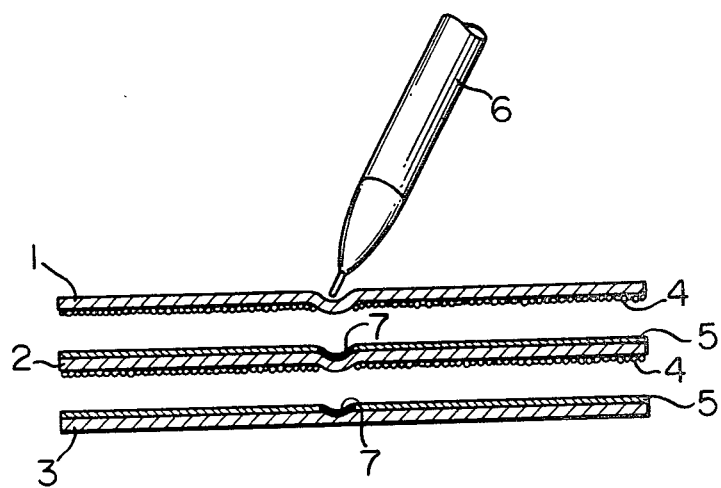

COLOR-DEVELOPING SHEET FOR PRESSURE-SENSITIVE RECORDING SHEETS

BACKGROUND OF THE INVENTION

This invention relates to a pressure-sensitive recording sheet, and more specifically, to a color-developing sheet for pressure-sensitive recording sheets which contains a novel color developing agent.

Pressure-sensitive recording sheets are also known as carbonless copying paper. They produce a color upon the application of a mechanical or impact pressure by writing or by pounding a typewriter, thus permitting duplication of several copies simultaneously. The color is based on a color forming reaction between an electron-donating colorless dye and an electron-accepting color developer.

The structure of a pressure-sensitive recording sheet and the mechanism of color formation are illustrated generally with reference to the accompanying drawing. The back surface of each of a top (CB: Coated Back) sheet 1 and a middle (CFB: Coated Front and Back) sheet 2 is coated with microcapsules 4 having a diameter of several microns to ten and several microns and composed of a shell of a polymeric film such as gelatin and a solution of a colorless color-forming pressure-sensitive dye in an involatile oil enclosed therein. The surface of each of the middle CFB sheet 2 and the bottom (CF: Coated Front) sheet 3 is coated with a layer 5 containing a color developing agent having the property of reacting with the colorless dye upon contact therewith and thus producing a color. A sheet coated with a coating composition containing a color developer, such as the CFB sheet and the CF sheet, is called a color-developing sheet. When a localized pressure is applied by a writing instrument 6 (or a typewriter or the like) to a pressure-sensitive recording sheet composed of a multiply structure of CB sheet 1, CFB sheet 2 and CF sheet 3 so that the microcapsule-coated surface faces the surface coated with the color developer-containing layer 5, the microcapsules 4 under the applied pressure break and the solution of the colorless dye moves to the color developer-containing layer 5. Thus, the dye reacts with the color developer to from a colored image 7 in the desired pattern of recording. In the pressure-sensitive recording sheet illustrated in the drawing, only the CFB sheet is interposed between the CB sheet 1 and the CF sheet 3, but if desired, two or more CFB sheets may be interposed.

Conventionally known electron-accepting color developing agents include (1) inorganic solid acids such as acid clay (Fuller's earth) or attapulgite, (2) substituted phenols and diphenols, (3) p-substituted phenol formaldehyde polymers, and (4) metal salts of aromatic carboxylic acids. These color-developing agents, however, are not entirely satisfactory. For example, the inorganic solid acids adsorb gases or moisture in the air and cause yellowing of the sheet or are deteriorated in color-forming property. With the substituted phenols and diphenols, the ultimate density of color is unsufficient. The p-substituted phenol formaldehyde polymers (for example, p-phenyl phenol novolak resin) have superior color-forming properties, but have the defect that the coated sheet undergoes yellowing upon exposure to sunlight. The aromatic carboxylic acid metal salts are superior in color-forming ability, light fastness of the colored image and resistance to yellowing under light, but their water resistance and plasticizer resistance are not entirely satisfactory.

It is a first object of this invention to provide a color-developing sheet which exhibits an equivalent or higher color-developing ability to or than developing sheets containing conventional inorganic solid acids or p-phenylphenol novolak resin as a color developing agent, and which give colors having superior water resistance and plasticizer resistance.

A second object of this invention is to provide a color developing sheet which gives a colored image having superior light fastness and undergoing little decrease in density with time, and whose tendency to yellowing under sunlight or the like is drastically reduced.

A third object of this invention is to provide a color-developing sheet which lends itself to very advantageous handling and storage.

According to this invention, there is provided a color-developing sheet for pressure-sensitive recording sheets, said color-developing sheet comprising as a color-developing agent at least one 2,2'-bisphenolsulfone nickel salt selected from compounds of the following formula

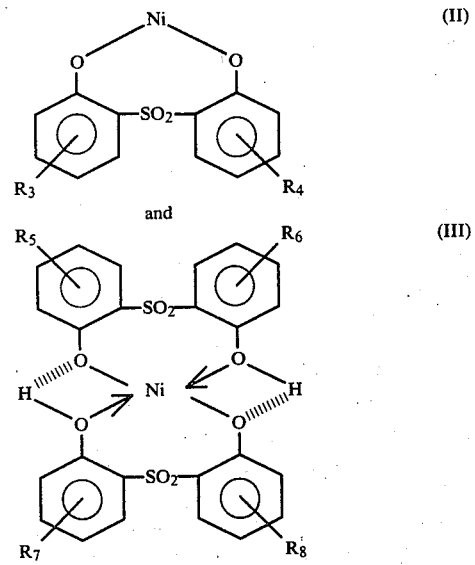

wherein $R_3$, $R_4$, $R_5$, $R_6$, $R_7$ and $R_8$ are identical or different, and represent a hydrogen atom, a halogen atom, an alkyl group containing 1 to 10 carbon atoms, a cycloalkyl group containing 3 to 10 carbon atoms, an aralkyl group containing 7 to 11 carbon atoms, or a phenyl group, or a mixture of at least one 2,2'-bisphenolsulfone nickel salt of the above formulae (II) and (III) and at least one 2,2'-bisphenolsulfone zinc salt of the following formula

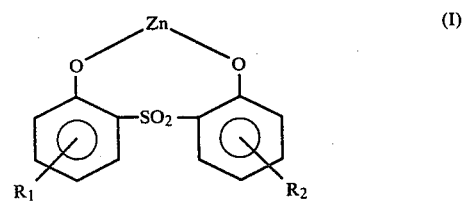

wherein $R_1$ and $R_2$ are the same as $R_3$ through $R_8$ defined above.

In a preferred embodiment, the present invention provides a color-developing sheet for pressure-sensitive recording sheets, said color-developing sheet comprising both the aforesaid 2,2'-bisphenolsulfone metal salt and at least one polyvalent metal compound selected from the group consisting of oxides, hydroxides and carbonates of zinc, magnesium, aluminum, lead, titanium, calcium, cobalt, nickel, manganese and barium.

The 2,2'-bisphenolsulfone metal salts of general formulae (I), (II) and (III) are known compounds. However, it has not been known that these compounds form a color upon contact with a colorless pressure-sensitive dye to form a colored image having superior fastness characteristics, and are thus suitable as a color-developing agent for pressure-sensitive recording sheets. In addition, it has been difficult to anticipate the suitability of the 2,2'-bisphenolsulfone metal salts as a color-developing agent.

Free bisphenolsulfone, a precursor for the metal salts of formulae (I), (II) and (III), has been found to have little or no color-forming ability when used as a color-developing agent for pressure-sensitive recording sheets.

The color-developing sheet of this invention containing the metal salt of formulae (I), (II) or (III) has an equivalent or greater color-forming ability to or than color-developing sheets containing inorganic solid acids or p-phenyl phenol novolak resin as a color-developing agent, and the image formed has good resistance to fading under the action or water, plasticizers, light, etc. In particular, a color-developing sheet containing a nickel salt of 2,2'-bisphenolsulfone as a color-developing agent gives an image which has very good resistance to light (i.e. very good light fastness). Thus, this sheet is better than a sheet comprising as a color-developing agent an aromatic carboxylic acid metal salt which proves to be relatively good among the color-developing agents heretofore suggested. The color-developing sheet of this invention also has much improved resistance to yellowing under exposure of sunlight or the like, and lends itself to very advantageous handling and storage.

DETAILED DESCRIPTION OF PREFERRED EMBODIMENTS

The subject matter of this invention is a color-developing sheet for pressure-sensitive recording sheets, said color-developing sheet comprising as a color-developing agent at least one 2,2'-bisphenolsulfone nickel salt selected from compounds of the following formula

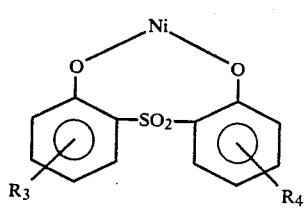

(II)

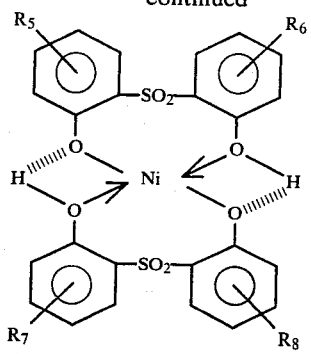

(III)

wherein $R_3$, $R_4$, $R_5$, $R_6$, $R_7$ and $R_8$ are identical or different, and represent a hydrogen atom, a halogen atom, an alkyl group containing 1 to 10 carbon atoms, a cycloalkyl group containing 3 to 10 carbon atoms, an aralkyl group containing 7 to 11 carbon atoms, or a phenyl group, or a mixture of at least one 2,2'-bisphenolsulfone nickel salt of the above formulae (II) and (III) and at least one 2,2'-bisphenolsulfone zinc salt of the following formula

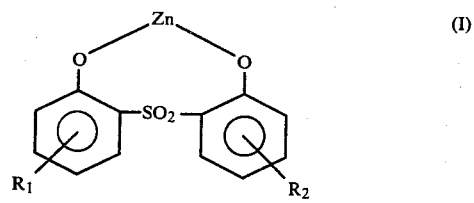

(I)

wherein $R_1$ and $R_2$ are the same as $R_3$ through $R_8$ defined above. 2,2'-bisphenolsulfone used to produce the metal salt of formula (I), (II) or (III) is produced, for example, by (i) oxidizing with hydrogen peroxide a 2,2'-bisphenol sulfide compound obtained by the reaction of a p-substituted phenol with sulfur dichloride, or (ii) oxidizing with hydrogen peroxide a 2,2'-bisphenol sulfoxide compound obtained by the reaction of a p-substituted phenol with thionyl chloride. Examples of the p-substituted phenol that can be used in the above reaction include p-halophenols such as p-chlorophenol and p-bromophenol; p-alkylphenols such as p-cresol, p-amylphenol, p-octylphenol, p-tertiary butylphenol and p-nonylphenol; p-cycloalkylphenols such as p-cyclohexylphenol; p-(α,α-dimethylbenzyl)phenol; and p-phenylphenol. Among these, p-octylphenol, p-nonylphenol, p-cyclohexylphenol, and p-(α,α-dimethylbenzyl)phenol are preferred. These p-substituted phenols may be used alone or in combination with one another. When two or more p-substituted phenols are used, there can be obtained a mixture composed of two or more 2,2'-bisphenolsulfones having the formula

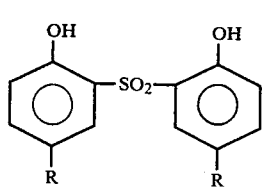

in which two R groups are different from each other.

Some known methods can be applied to the production of the metal salt of formula (I), (II) or (III) from the resulting 2,2'-bisphenolsulfone or its mixture.

One method comprises reacting an alkali metal salt of the 2,2'-bisphenolsulfone with a water-soluble zinc salt or nickel salt in a solvent capable of dissolving both. According to this method, the 2,2'-bisphenolsulfone is first reacted with an alkali metal hydroxide or alkoxide to form the alkali metal salt of 2,2'-bisphenolsulfone or its solution in water, an alcohol or in a mixture of water and an alcohol. Then, the product is reacted with the water-soluble zinc or nickel salt.

Specifically, when the 2,2'-bisphenolsulfone zinc or nickel salt of formula (I) or (II) is to be produced, at least 2 moles of the alkali metal hydroxide or alkoxide and at least one mole of the water-soluble zinc or nickel salt are used per mole of the 2,2'-bisphenolsulfone. In the production of the 2,2'-bisphenolsulfone nickel salt of formula (III), 1 mole of the alkali metal hydroxide or alkoxide and 0.5 mole of the water-soluble nickel salt are used per mole of 2,2'-bisphenolsulfone. Examples of the water-soluble zinc salt that can be used are inorganic acid salts such as zinc chloride, zinc sulfate and zinc nitrate and organic acid salts such as zinc oxalate and zinc acetate. Examples of the water-soluble nickel salt that can be used include inorganic acid salts such as nickel chloride, nickel sulfate and nickel nitrate, and organic acid salts such as nickel oxalate and nickel acetate.

The metal salt of formula (I), (II) or (III) can also be produced by reacting 2,2'-bisphenolsulfone with an organic acid salt such as zinc oxalate, zinc acetate, nickel oxalate or nickel acetate in an organic solvent at an elevated temperature. Useful organic solvents for this reaction include methanol, ethanol, butanol, acetone, benzene, toluene, and methylene chloride. It is especially effective to dissolve the 2,2'-bisphenolsulfone compound in such a solvent.

To produce a color-developing agent composed of a mixture of the zinc salt and the nickel salt, it is possible to first produce the zinc salt of formula (I) and the nickel salt of formula (II) or (III) and then mixing these salts. Or it may be prepared by reacting the 2,2'-bisphenolsulfone compound with a mixture of a water-soluble zinc salt and a water-soluble nickel salt.

The metal salts of general formulae (I), (II) and (III) are used as color-developing agents either alone or in combination with each other according to the purpose of use.

When the light fastness of a colored image is particularly required, it is desirable to use as a color-developing agent a mixture of the 2,2'-bisphenolsulfone zinc salt of general formula (I) and at least one of the 2,2'-bisphenolsulfone nickel salts of general formulae (II) and (III). The mixing ratio of the zinc salt to the nickel salt in this case is generally from 20:1 to 1:100, preferably from 10:1 to 1:10, especially preferably from 5:1 to 1:3, by weight. When the mixing ratio is within the above-specified range, color-developing sheets having a well balanced combination of the properties required of a pressure-sensitive recording sheet can be obtained.

The color-developing agent in accordance with this invention can be used jointly with known color-developing agents, such as inorganic solid acids (e.g. activated acid clay), organic polymers (e.g., phenol-formaldehyde resin), and aromatic carboxylic acid metal salts, without any deleterious effect.

In one preferred embodiment of this invention, 0.01 to 10 parts by weight, preferably 0.2 to 5 parts by weight, per part by weight of the color-developing agent of at least one polyvalent metallic compound selected from the group consisting of oxides, hydroxides and carbonates of zinc, magnesium, aluminum, lead, titanium, calcium, cobalt, nickel and manganese is coated together with the color-developing agent on a sheet. Examples of the polyvalent metal compounds are zinc oxide, magnesium oxide, aluminum oxide, calcium oxide, lead oxide, titanium oxide, manganese oxide, magnesium hydroxide, aluminum hydroxide, calcium hydroxide, zinc hydroxide, and calcium carbonate. When these polyvalent metal compounds are used, the resulting color-developing sheet has improved resistance to yellowing under light, and the rate of color development becomes faster and the color density increases. Moreover, the light fastness, plasticizer resistance and storage stability of the image formed are improved at the same time. Among the aforesaid polyvalent metal compounds, zinc oxide is most practical.

The color-developing sheet of this invention can be prepared by various methods. A typical method comprises coating a sheet such as paper with a water-base coating color containing the color-developing agent suspended therein. The coating color is conditioned to have a suitable viscosity and suitable coating characteristics by incorporating a kaolin clay, calcium carbonate, starch, etc. in a synthetic or natural latex, and desirably contains 10 to 70% by weight of the color-developing agent based on the total solids content. When the content of the color-developing agent is less than 10% by weight, the color-developing agent cannot exhibit sufficient color-forming properties. When it exceeds 70% by weight, the characteristics of the surface of the resulting color-developing sheet are deteriorated. The amount of the coating color to be coated on the base sheet is at least 0.5 g/m$^2$, preferably 1 to 10 g/m$^2$, as solids content. In other words, at least 0.05 g/m$^2$, preferably 0.1 to 7 g/m$^2$, of the color-developing agent is applied to the sheet.

The color-developing sheet of this invention can also be produced by an alternative method which comprises dissolving or suspending the color-developing agent in an organic solvent such as alcohols, hydrocarbons or ketones, optionally incorporating a kaolin clay, calcium carbonate, etc., and coating the resulting solution or suspension on a sheet such as paper. The amount of the coating solution or suspension is at least 0.05 g/m$^2$, preferably 0.1 to 7 g/m$^2$, as the color-developing agent.

Still another method for producing the color-developing sheet of this invention comprises incorporating the color-developing agent into a sheet-forming stock, and subjecting the mixture to a sheet-forming process.

The amount of the color-developing agent can be reduced in the present invention, and the concentration, viscosity, etc. of the coating composition can be varied over relatively wide ranges. Accordingly, both on-machine coating and off-machine coating are possible, and great advantages can be obtained not only in the properties of the color-developing sheet, but also in the process steps of sheet production.

The following Examples specifically illustrate the present invention.

SYNTHESIS EXAMPLE 1

In a mixture of carbon tetrachloride and n-hexane, p-tert-octyl phenol was reacted with sulfur dichloride to form 2,2'-bis(p-tert-octylphenol)sulfide. The sulfide was oxidized with hydrogen peroxide in glacial acetic acid to form 2,2'-bis(p-tert-octylphenol)sulfone. Recrystallization from carbon tetrachloride/n-hexane afforded a purified product having a melting point of 142° to 144° C.

Then, 9.48 g (0.02 mole) of the resulting 2,2'-bisphenolsulfone was added to a solution of 1.6 g (0.04 mole) of sodium hydroxide in 100 ml of ethyl alcohol. The solution was stirred for 1 hour under reflux, and then cooled to 30° C. A solution of 2.73 g (0.02 mole) of zinc chloride in 50 ml of ethyl alcohol was added, and the mixture was refluxed for 1 hour. The reaction mixture was poured into 500 ml of ice water. The precipitated white crystals were collected by filtration, and dried to afford 10.6 g of 2,2'-bis(p-tert-octylphenol)sulfone zinc salt (to be referred to as compound No. 1) corresponding to general formula (I).

SYNTHESIS EXAMPLE 2

11.85 g (0.025 mole) of the 2,2'-bis(p-tert-octylphenol)sulfone used in Synthesis Example 1 was dissolved in a solution of 2.0 g (0.05 mole) of sodium hydroxide in 100 ml of ethyl alcohol. The solution was added dropwise to a solution of 5.94 g (0.025 mole) of nickel chloride hexahydrate in 80 ml of ethyl alcohol. After the addition, the mixture was stirred for 2 hours under reflux, and then cooled. The resulting mixture was poured into 1500 ml of water. The pale green crystals precipitated were collected by filtration, and dried to afford 12.2 g of 2,2'-bis(p-tert-octylphenol)sulfone nickel salt (to be referred to as compound No. 2) corresponding to general formula (II).

SYNTHESIS EXAMPLE 3

Pale yellow 2,2'-bis[p-(α,α-dimethylbenzyl)phenol] sulfone was prepared in the same way as in Synthetic Example 1 using p-(α,α-dimethylbenzyl)phenol instead of the p-tert-octylphenol. Then, 12.2 g (0.025 mole) of the resulting 2,2'-bisphenolsulfone was added to a solution of 2.0 g (0.05 mole) of sodium hydroxide in 50 ml of methyl alcohol. The solution was added to a solution of 6.6 g (0.025 mole) of nickel sulfate hexahydrate in 80 ml of methyl alcohol. The mixture was stirred at 25° C. for 6 hours, and poured into 1 liter of ice water. The precipitated gray green crystals were collected by filtration, and dried to afford 11.5 g of 2,2'-bis[p-(α,α-dimethylbenzyl)phenol] sulfone nickel salt (to be referred to as compound No. 3) corresponding to general formula

SYNTHESIS EXAMPLE 4

Pale yellow 2,2'-bis(p-tert-butylphenol)sulfone was prepared in the same way as in Synthesis Example 1 using p-tert-butylphenol.

To a solution of 1.38 g (0.06 mole) of metallic sodium in 180 ml of ethyl alcohol was added 14.2 g (0.03 mole) of the aforesaid 2,2'-bisphenolsulfone. The mixture was stirred for 1 hour under reflux, and then cooled to 30° C. The reaction mixture was added to a solution of 4.09 g of zinc chloride in 100 ml of ethyl alcohol. The mixture was stirred for 4 hours at 30° C. The precipitated crystals were separated by filtration, and ethyl alcohol was distilled off under reduced pressure from the filtrate to afford 13.6 g of pale yellow crystals of 2,2'-bis(p-tert-butylphenol)sulfone zinc salt (to be referred to as compound No. 4) corresponding to general formula (I).

SYNTHESIS EXAMPLE 5

2,2'-bis(p-tert-amylphenol)sulfone nickel salt (to be referred to as compound No. 5) corresponding to general formula (II) was prepared in the same way as in Synthesis Example 2 using p-tert-amylphenol.

SYNTHESIS EXAMPLE 6

In dichloroethane, 2 moles of p-cyclohexylphenol was reacted with 1 mole of thionyl chloride to form 2,2'-bis(p-cyclohexylphenol)sulfoxide. The product was then oxidized with hydrogen peroxide in glacial acetic acid to form 2,2'-bis(p-cyclohexylphenol)sulfone. Recrystallization from carbon tetrachloride afforded white crystal having a melting point of 176° to 178° C. Using the white crystals, 2,2'-bis(p-cyclohexylphenol)sulfone nickel salt (to be referred to as compound No. 6) corresponding to general formula (II) was prepared in the same way as in Synthesis Example 2.

SYNTHESIS EXAMPLE 7

Using p-chlorophenol, 2,2'-bis(p-chlorophenol)sulfone nickel salt (to be referred to as compound No. 7) corresponding to general formula (II) was prepared in the same way as in Synthesis Example 2.

SYNTHESIS EXAMPLE 8

Pale green 2,2'-bis(p-tert-octylphenol)sulfone nickel salt (11.5 g) (to be referred to as compound No. 8) was prepared by operating in the same way as in Synthesis Example 2 except that 1.0 g (0.025 mole) of sodium hydroxide and 2.97 g (0.0125 mole) of nickel chloride were used.

SYNTHESIS EXAMPLE 9

Using p-nonylphenol, 2,2'-bis(p-nonylphenol)sulfone as a pale brown resinous substance was prepared in the same way as in Synthesis Example 2.

Then, 12.55 g (0.025 mole) of 2.2'-bisphenolsulfone was added to a solution of 2.0 g (0.05 mole) of sodium hydroxide in 100 ml of methyl alcohol. The mixture was stirred for 1 hour under reflux, and then cooled to 30° C. A solution of 2.73 g (0.02 mole) of zinc chloride and 1.19 g (0.005 mole) of nickel chloride in 100 ml of methyl alcohol was added to the resulting mixture, and the mixture was refluxed for 1 hour. The product was poured into 1 liter of ice water. The white crystals precipitated were collected by filtration, and dried to afford a mixture composed of 2,2'-bis(p-nonylphenol)sulfone zinc salt corresponding to general formula (I) and 2,2'-bis(p-nonylphenol)sulfone nickel salt corresponding to general formula (II) (to be referred to as mixture A).

SYNTHESIS EXAMPLE 10

In benzene, 0.5 mole of p-tert-octylphenol and p-(α,α-dimethylbenzyl)phenol were reacted with 0.5 mole of sulfur dichloride. The solvent was removed by steam distillation, and the reaction product was oxidized with hydrogen peroxide to obtain a mixture of the corresponding bis(p-substituted phenol)sulfones. The mixture was found to be a mixture of three kinds of sulfone by high-speed liquid chromatography and thin-layer chromatography. By operating in the same way as in Synthesis Example 2 using this 2,2'-bisphenolsulfone mixture, there was obtained a mixture of 2,2'-bis[p-(α,α-dimethylbenzyl)phenol]sulfone nickel salt, 2,2'-bis(p-tert-octylphenol)sulfone nickel salt and 2-(p-tert-octylphenol)-2'-[p-(α,α-dimethylbenzyl)phenol]sulfone nickel salt corresponding to general formula (II) (to be referred to as mixture B).

EXAMPLES 1 TO 10

Using each of compounds Nos. 1 to 8 and mixture A and B obtained in Synthesis Examples 1 to 10, as a color-developing agent, a suspension of the following formulation was prepared by means of a sand grinding mill.

| | |
|---|---|
| Color-developing agent | 24.5 parts by weight |
| Sodium ligninsulfonate | 3.0 parts by weight |
| Water | 42.5 parts by weight |

A coating composition of the following formulation was prepared by using the above suspension.

| | |
|---|---|
| Suspension | 50 parts by weight |
| Kaolin | 100 parts by weight |
| Styrene/butadiene latex (concentration 50%) | 15 parts by weight |
| Oxidized starch | 15 parts by weight |
| Water | 180 parts by weight |

The coating composition was coated on a sheet of fine paper and dried so that the amount of the coating composition applied was 6 g/m² upon drying. Thus, a color-developing sheet was obtained.

EXAMPLE 11

A suspension having the following formulation was prepared by means of a sand grinding mill using the mixture A obtained in Synthesis Example 9 as a color-developing agent.

| | |
|---|---|
| Color developing agent | 24.5 parts by weight |
| Sodium sulfonate of naphthalene-formaldehyde condensate | 2.0 parts by weight |
| Water | 42.5 parts by weight |

A coating composition having the following formulation was prepared from the suspension.

| | |
|---|---|
| Suspension | 50 parts by weight |
| Zinc oxide | 20 parts by weight |
| Kaolin | 80 parts by weight |
| Styrene/butadiene latex (concentration 50%) | 15 parts by weight |
| Oxidized starch | 15 parts by weight |
| Water | 180 parts by weight |

The coating composition was coated on a sheet of fine paper, and dried so that the amount of the coating composition was 6 g/m² upon drying. Thus, a color-developing sheet was obtained.

EXAMPLE 12

A color-developing sheet was obtained in the same way as in Example 11 except that magnesium oxide was used instead of zinc oxide.

EXAMPLE 13

A color-developing sheet was obtained in the same way as in Example 11 except that aluminum hydroxide was used instead of zinc oxide.

COMPARATIVE EXAMPLE 1

A suspension and a coating composition were prepared in accordance with the same formulations as in Example 1 using 2,2'-bis(p-tert-octylphenol)sulfone which is a precursor of the 2,2'-bis(p-tert-octylphenol)sulfone zinc salt (compound No. 1) obtained in Synthesis Example 1. The coating composition was coated on a sheet of fine paper and dried so that the amount of the coating composition was 6 g/m² upon drying. Thus, a color-developing sheet was obtained.

COMPARATIVE EXAMPLE 2

A color-developing sheet was prepared in the same way as in Comparative Example 1 using 2,2'-bis[p-(α,α-dimethylbenzyl)phenol]sulfone, which is a precursor of the 2,2'-bis[p-(α,α-dimethylbenzyl)phenol]sulfone nickel salt (compound No. 3) obtained in Synthesis Example 3.

COMPARATIVE EXAMPLE 3

A glass reactor was charged with 170 g of p-phenylphenol, 22.5 g of 80% para-formaldehyde, 2.0 g of p-toluenesulfonic acid and 200 g of benzene, and with stirring, the contents were heated. While water generated as a result of the reaction was distilled off out of the reactor as an azeotrope with benzene, they were reacted at 70° to 80° C. for 2 hours. Then, 320 g of a 10% aqueous solution of sodium hydroxide was added, and benzene was distilled off by steam distillation. Dilute sulfuric acid was added dropwise, and the precipitated p-phenylphenol/formaldehyde polymer was collected by filtration, washed with water, and dried to afford 176 g of a white powder. A color-developing sheet was produced in the same way as in Comparative Example 1 using the resulting p-phenylphenol/formaldehyde polymer.

COMPARATIVE EXAMPLE 4

A color-developing sheet was prepared in the same way as in Comparative Example 1 except using zinc 3-[4'-(α,α-dimethylbenzyl)phenyl]-5-(α,α-dimethylbenzyl)salicylate.

TEST EXAMPLES

The properties of the color-developing sheets produced in Examples 1 to 13 and Comparative Examples 1 to 4 were tested by the following methods. The results are tabulated below.

(1) Color-developing rates of the color-developing sheet

A commercially available CB sheet (NW-50T, a product of Jujo Paper Co., Ltd.) containing crystal violet lactone as a main pressure-sensitive dye and a sample color-developing sheet are laid so that the coated surface of the sheets contacted each other. A pressure is applied to the multiply sheet by an electric typewriter to form a cobalt blue color. The reflectance $I_o$ of the sheet before color development, the reflectance $I_1$ of the sheet two minutes after color development, and the reflectance $I_2$ of the sheet 24 hours after color formation are measured by using a Hunter Reflectmeter (using an amber filter). The initial color-developing rate ($J_1$) and the ultimate color-developing rate ($J_2$) are calculated in accordance with the following equations.

$$J_1 = \frac{I_o - I_1}{I_o} \times 100 \, (\%)$$

$$J_2 = \frac{I_o - I_2}{I_o} \times 100 \, (\%)$$

Higher initial and ultimate color-developing rates are preferred.

(2) Retention of color intensity (Light-fade resistance)

The color-developing sheet having a color formed by the method described in (1) is exposed to a fade-o-meter for 2 hours and 6 hours, respectively. The color-developing rates of the sheets are calculated in the same way as in (1) above as $J_3$ and $J_4$. The reaction of color is calculated in accordance with the following equations.

$$\text{Color retention after 2 hours exposure} = \frac{J_3}{J_2} \times 100 \, (\%)$$

$$\text{Color retention after 6 hour exposure} = \frac{J_4}{J_2} \times 100 \, (\%)$$

Higher color retention values are preferred.

(3) Retention of whiteness (Resistance to yellowing)

The color-developing sheet before color formation is exposed to a fade-o-meter for 6 hours. The reflectance $K_1$ of the sheet before the exposure, and its reflectance $K_2$ after the exposure are measured by using a Hunter Reflectmeter (using a blue filter). The retention of whiteness (H) is calculated in accordance with the following equation.

$$H = (K_2/K_1) \times 100 \, (\%)$$

Higher whiteness retention values show less yellowing of the sheet under light.

(4) Plasticizer resistance of colored image

A small amount of dioctyl phthalate (a plasticier for vinyl chloride resins) is coated on the colored surface of the color-developing sheet after color formation by the method described in (1) above. A change in the density of the color was observed with unaided eyes immediately after coating and two weeks after coating.

(5) Water resistance to colored image

The color-developing sheet after color formation by the method described in (1) is dipped in water. A change in the density of the color was observed with unaided eyes two 1 hours after dipping.

| Color-developing sheet (*) | Color developing agent | | Color developing rates (%) | | Retention of color (%) | | Whiteness retention (%) | Plasticizer resistance of colored image | | Water resistance of colored image after 2 hour dipping |
|---|---|---|---|---|---|---|---|---|---|---|
| | Compound No. | Amount (parts by weight) | $J_1$ | $J_2$ | 2 hrs | 6 hrs | | Immediately after coating | 2 weeks after coating | |
| Ex. 1 | 2 | 24.5 | 39.5 | 46.5 | 92.0 | 82.5 | 98.0 | No decrease in color density | Slight decrease in color density | No decrease in color density |
| Ex. 2 | 3 | 24.5 | 30.2 | 47.5 | 87.0 | 79.8 | 97.1 | No decrease in color density | Slight decrease in color density | No decrease in color density |
| Ex. 3 | 1 & 3 | 19.6 4.9 | 38.0 | 48.0 | 58.8 | 23.4 | 92.0 | No decrease in color density | Slight decrease in color density | No decrease in color density |
| Ex. 4 | 3 & 4 | 19.6 4.9 | 30.3 | 47.5 | 83.0 | 68.6 | 95.7 | No decrease in color density | Slight decrease in color density | No decrease in color density |
| Ex. 5 | 5 | 24.5 | 35.9 | 44.3 | 84.0 | 61.8 | 93.5 | No decrease in color density | Slight decrease in color density | No decrease in color density |
| Ex. 6 | 1 & 8 | 12.25 12.25 | 35.6 | 47.5 | 73.2 | 46.6 | 94.1 | No decrease in color density | Slight decrease in color density | No decrease in color density |
| Ex. 7 | 6 | 24.5 | 27.1 | 45.5 | 90.3 | 79.6 | 96.5 | No decrease in color density | Slight decrease in color density | No decrease in color density |
| Ex. 8 | 7 | 24.5 | 29.2 | 43.0 | 88.5 | 75.3 | 93.2 | No decrease in color density | Slight decrease in color density | No decrease in color density |
| Ex. 9 | mixture A | 24.5 | 39.4 | 45.3 | 68.4 | 36.9 | 92.5 | No decrease in color density | Slight decrease in color density | No decrease in color density |
| Ex. 10 | mixture B | 24.5 | 41.2 | 47.0 | 90.1 | 81.5 | 98.0 | No decrease in color density | Slight decrease in color density | No decrease in color density |
| Ex. 11 | mixture A | 24.5 | 40.6 | 47.1 | 75.0 | 43.3 | 96.2 | No | Slight | No decrease |

-continued

| Color-developing sheet (*) | Color developing agent Compound No. | Amount (parts by weight) | Color developing rates (%) J₁ | J₂ | Retention of color (%) 2 hrs | 6 hrs | Whiteness retention (%) | Plasticizer resistance of colored image Immediately after coating | 2 weeks after coating | Water resistance of colored image after 2 hour dipping |
|---|---|---|---|---|---|---|---|---|---|---|
| Ex. 12 | mixture A | 24.5 | 40.0 | 46.3 | 71.1 | 38.6 | 93.1 | decrease in color density No decrease in color density | decrease in color density Slight decrease in color density | in color density No decrease in color density |
| Ex. 13 | mixture A | 24.5 | 40.1 | 46.0 | 71.0 | 39.3 | 92.7 | No decrease in color density | Slight decrease in color density | No decrease in color density |
| CEx. 1 | Free sulfone | 24.5 | no color formed | — | — | — | — | — | — | — |
| CEx. 2 | Free sulfone | 24.5 | no color formed | — | — | — | — | — | — | — |
| CEx. 3 | Known color developing agent | 24.5 | 41.0 | 47.0 | 50.7 | 10.7 | 82.0 | Marked decrease in color density | Marked decrease in color density | No decrease in color density |
| CEx. 4 | Known color developing agent | 24.5 | 23.5 | 46.2 | 68.3 | 13.4 | 90.0 | Slight decrease in color density | Marked decrease in color density | No decrease in color density |

*Ex. = Example;
CEx. = Comparative Example

It can be seen from the table that the color-developing sheets of this invention have a marked improvement in color-forming properties than the color-developing sheets of Comparative Examples 1 and 2 (prepared in the same way as in Example 1 using free sulfones which are precursors of the color-developing agents of the present invention). In other words, while the free sulfones have no color-forming properties, the nickel salts thereof or the mixture of the nickel salt and zinc salt have very good color-forming properties. Furthermore, the color-developing sheets of this invention have equivalent or slightly better color-forming properties (the color-developing rate) and water resistance to or than the color-developing sheets of Comparative Examples 3 and 4 (color-developing sheets containing known color developing-agents), but have much better light fading resistance (color retention), resistance to yellowing under light (whiteness retention) and plasticizer resistance than the latter.

Since the color produced by the color-developing sheet of this invention is stable to light and plasticizers or the like and scarcely undergoes a decrease in density, it can be used in applications for which conventional color-developing sheets are unsuitable because of the need for long-term storage stability. Hence, the color-developing sheet of this invention has a very great practical significance.

What we claim is:

1. A color-developing sheet for pressure-sensitive recording sheets, said color-developing sheet comprising a base sheet and associated therewith a color-developing agent comprising at least one 2,2'-bisphenolsulfone nickel salt selected from compounds of the following formula

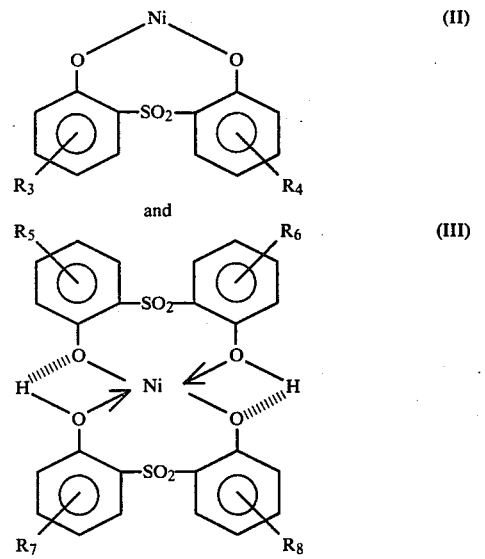

wherein $R_3$, $R_4$, $R_5$, $R_6$, $R_7$ and $R_8$ are identical or different, and represent a hydrogen atom, a halogen atom, an alkyl group containing 1 to 10 carbon atoms, a cycloalkyl group containing 3 to 10 atoms, an aralkyl group containing 7 to 11 carbon atoms, or a phenyl group, or a mixture of at least one 2,2'-bisphenolsulfone nickel salt of the above formulae (II) and (III) and at least one 2,2'-bisphenolsulfone zinc salt of the following formula.

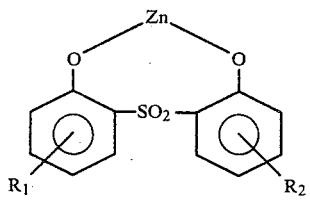 (I)

wherein $R_1$ and $R_2$ are the same as $R_3$ through $R_8$ defined above.

2. The color-developing sheet of claim 1 wherein the color-developing agent is at least one 2,2'-bisphenolsulfone nickel salt of general formulae (II) and (III).

3. The color-developing sheet of claim 1 wherein the color-developing agent is a mixture of at least one 2,2'-bisphenolsulfone zinc salt of general formula (I) and at least one 2,2'-bisphenolsulfone nickel salt of general formulae (II) and (III).

4. The color-developing sheet of claim 3 wherein the weight ratio of the zinc salt to the nickel salt is from 20:1 to 1:100.

5. The color-developing sheet of claim 4 wherein the weight ratio of the zinc salt to the nickel salt is from 10:1 to 1:10.

6. The color-developing sheet of claim 4 wherein the weight ratio of the zinc salt to the nickel salt is from 5:1 to 1:3.

7. The color-developing sheet of claim 1 or 3 wherein the 2,2'-bisphenolsulfone zinc salt or nickel salt is a product from at least one p-substituted phenol selected from the group consisting of p-halophenols, p-alkylphenols, p-cycloalkylphenols, p-(α,α-dimethylbenzyl) phenols and p-phenylphenol.

8. The color-developing sheet of any one of claims 1, 2 and 3 which further comprises at least one polyvalent metal compound selected from the group consisting of oxides, hydroxides and carbonates of zinc, magnesium, aluminum, lead, titanium, calcium, cobalt, nickel and manganese.

9. The color-developing sheet of claim 8 wherein the polyvalent metal compound is zinc oxide.

10. The color-developing sheet of claim 9 wherein the amount of the zinc oxide is from 0.01 to 10 parts by weight, per part by weight of the color-developing agent.

11. The color-developing sheet of claim 9 wherein the amount of the zinc oxide is from 0.2 to 5 parts by weight, per part by weight of the color-developing agent.

12. The color-developing sheet of claim 8 wherein the amount of the polyvalent metal compound is from 0.01 to 10 parts by weight, per part by weight of the color-developing agent.

13. The color-developing sheet of claim 8 wherein the amount of the polyvalent metal compound is from 0.2 to 5 parts by weight, per part by weight of the color-developing agent.

14. The color-developing sheet of claim 1 wherein the color-developing sheet comprises the base sheet and a layer of a coating composition containing said color-developing agent coated on said base sheet.

15. The color-developing sheet of claim 14 wherein the color-developing agent is applied to the base sheet in an amount of from 0.1 to 7 g/m².

16. The color-developing sheet of claim 15 wherein said coating further comprises from about 0.01 to 10 parts by weight of zinc oxide per part by weight of the color-developing agent.

17. The color-developing sheet of claim 1 wherein the color-developing agent is incorporated in said base sheet.

18. The color-developing sheet of claim 1 wherein the color-developing agent is 2,2'-bis(p-tert-octylphenol)sulfone nickel salt.

* * * * *

UNITED STATES PATENT AND TRADEMARK OFFICE
CERTIFICATE OF CORRECTION

PATENT NO. : 4,262,938

DATED : April 21, 1981

INVENTOR(S) : Akihiro Yamaguchi, et al.

It is certified that error appears in the above—identified patent and that said Letters Patent is hereby corrected as shown below:

Title page, item (75) should read

-- Akihiro Yamaguchi; Tadashi Kobayashi, both of Yokohama; Keizaburo Yamaguchi, Kawasaki; Hisamichi Murakami, Yokohama; Noboru Yamato, Tokyo; Akira Hasegawa, Tokyo, all of Japan --.

Signed and Sealed this

Twenty-second Day of June 1982

[SEAL]

Attest:

Attesting Officer

GERALD J. MOSSINGHOFF

Commissioner of Patents and Trademarks